United States Patent [19]

Barker et al.

[11] 4,229,970

[45] Oct. 28, 1980

[54] METHOD AND APPARATUS FOR MEASURING THE RHEOLOGICAL PROPERTIES OF AN EXTRUDABLE MATERIAL

[75] Inventors: Robert I. Barker, Cuyahoga Falls; David P. King, Akron, both of Ohio; Patrick F. Rice, Chesterfield, Mo.

[73] Assignee: Monsanto Company, St. Louis, Mo.

[21] Appl. No.: 1,136

[22] Filed: Jan. 5, 1979

[51] Int. Cl.³ ...................... G01N 11/04; G01B 11/08
[52] U.S. Cl. ........................................ 73/56; 264/40.2; 356/386
[58] Field of Search .................. 73/56, 15.4, 105; 264/22, 40.2, 176 R; 250/560; 356/386

[56] References Cited

U.S. PATENT DOCUMENTS

| | | | |
|---|---|---|---|
| 3,544,774 | 12/1970 | Peklenik | 73/105 X |
| 3,749,500 | 7/1973 | Carlson . | |
| 3,765,774 | 10/1973 | Petrohilos . | |
| 3,824,021 | 7/1974 | Axelrod et al. . | |
| 4,037,968 | 7/1977 | King et al. | 356/386 |
| 4,061,427 | 12/1977 | Fletcher et al. . | |
| 4,096,739 | 6/1978 | Barker et al. | 73/56 |
| 4,101,612 | 7/1978 | Barker et al. | 264/22 |
| 4,126,036 | 11/1978 | Nilan et al. | 73/105 |

OTHER PUBLICATIONS

Tokita, N. et al., *The Dependence of Processability on Molecular Weight Distribution of Elastomers*, in Rubber Chemistry and Technology, (46), pp. 1166–1187, 1973.

Vegvari, P. C. et al., *Measurement of Carbon Black Dispersion in Rubber by Surface Analysis*, in Rubber Chemistry and Technology, (51), pp. 817–839, 1978.

*Primary Examiner*—Gerald Goldberg
*Assistant Examiner*—Joseph W. Roskos
*Attorney, Agent, or Firm*—Gordon B. Seward

[57] ABSTRACT

The rheological properties of an extrudable material can be measured by extruding a strand of the material, measuring its diameter continuously, to give a series of diameter values, interpreting the variations in the strand diameter so as to characterize the surface of the strand, and deriving rheological data from the surface characteristics of the strand. The variations in the strand diameter can be interpreted as to peak-to-peak amplitude, average diameter value, the frequency of significant extreme values, standard deviations from a mean value, and the like. By means of these mathematical characterizations, the rheological behavior of the extrudable material can then be derived. The scorch behavior of a curable elastomer can be measured. The heterogeneity of a rubber compound can be described, or the macromolecular properties of a polymer can be measured (such as "gel", or degree of cross-linking.)

15 Claims, 14 Drawing Figures

$D = T \sin \theta \left(1 - \dfrac{\cos \theta}{N(\cos \theta')}\right)$   N = REFRACTIVE INDEX OF CUBE

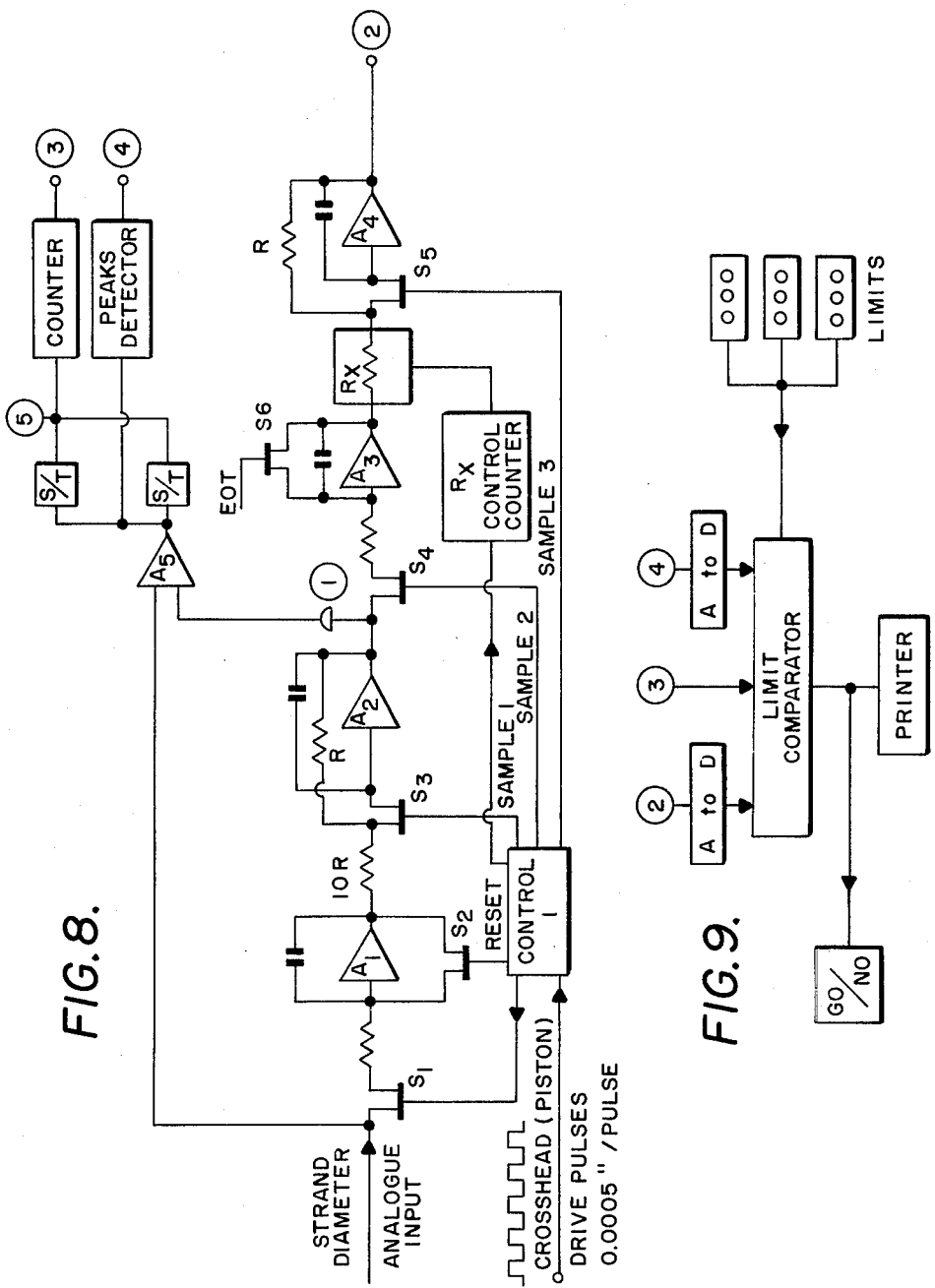

METHOD AND APPARATUS FOR MEASURING THE RHEOLOGICAL PROPERTIES OF AN EXTRUDABLE MATERIAL

BACKGROUND OF THE INVENTION

The invention relates to a method and apparatus for measuring the rheological properties of an extrudable material.

Rheological properties of a material are those which relate to the flow of the material, and are of importance in processing rubber and plastic materials. For example, in forming rubber or plastic articles, the articles are shaped by injection molding, transfer molding, compression molding, extrusion, and other processes, wherein a mass of flowable material is subjected to differential pressures so as to change its shape. The behavior of the material under different conditions of pressure, temperature and shear will determine the process equipment and techniques required to form the final article. Also, since the properties of the flowable material may vary from batch to batch it is desirable to be able to predict the rheological behavior of a batch before it is used in the production process.

A number of methods have been used to predict the rheological behavior of rubber or plastic materials, with varying degrees of success. The Mooney viscometer is widely used to measure the viscosity of natural and synthetic rubber polymers. This device employs a fixed stator and movable rotor with a small sample of rubber between them. The measure of the force required to move the rotor and shear the rubber sample is a measure of the viscosity of the rubber.

An improved device employing a conical disc imbedded in a rubber sample and oscillating over a small arc has given more insight into the rubber properties.

More recently, the Capillary Rheometer has been introduced, which extrudes a sample of polymer through an orifice. Stress-strain measurements at different shear rates and temperatures provide insight into the rheological behavior of the polymer at higher shear rates. As a further adjunct to the Capillary Rheometer, the diameter of the polymer extrudate has been optically measured, to yield die swell data.

Despite the various known methods for evaluating the rheological behavior of rubber and plastic materials a need exists for a method and apparatus which can quickly and accurately produce a wide variety of rheological data from a small sample of the material, and provide predictions of the processing behavior for all steps of production.

Variations in "raw", or uncompounded polymer from batch to batch can result from differences in the macrostructure of the polymer, such as its molecular weight distribution, degree of branching, and content of "gel" (less soluble portions). These variations can result in processing differences throughout the entire production cycle.

When compounding ingredients, such as vulcanizing or cross-linking agents, antidegradants, fillers and plasticizers are added to a rubber or plastic material, its rheological behavior is changed. Inadequate mixing of these materials, especially fillers, can cause heterogeneity, which often will negatively affect the processing of the compounded material.

In the case of plastic or rubber materials which are cross-linkable (i.e., thermosetting) another potential processing problem is introduced when the cross-linking agent is added. If the cross-linking process begins prematurely, the probability of processing difficulties is greatly multiplied. Since it is usually desirable to have cross-linking occur as rapidly as possible once the material assumes its final form, the cross-linking rate must be carefully controlled at a rate neither too slow nor too fast. In rubber compounding the effect of cross-linking on processing is known as "scorch". Known methods for evaluating the scorch time of a compound yield results indicative of the onset of cross-linking as it is evidenced in the bulk of the material, by a viscosity increase. Small localized scorch, sometimes termed "micro-scorch" may occur because of imperfect dispersion, and usually happens before the bulk scorch effects are noticed. A measure of the incidence and severity of micro-scorch not obtainable by known scorch tests would be of great value to rubber processers.

In summary, the need exists for a method and apparatus whereby the rheological properties of a rubber or plastic material in all stages of its processing could be accurately, easily and quickly obtained by testing a small sample of the material.

SUMMARY OF THE INVENTION

It is an object of the present invention to provide a method whereby a sample of an extrudable material could be analyzed to predict its processing behavior in the production of a shaped article.

It is a further object of the present invention to provide an apparatus wherein an extrudable material could be subjected to a rapid accurate measurement of its rheological behavior.

These and other objects are realized by the method and apparatus of the invention which extrudes a continuous strand of the extrudable material under controlled conditions of time and temperature, measures the diameter of the strand to provide a plurality of diameter values, interprets variations in the strand diameter values so as to characterize the surface of the strand, and derives rheological data from the surface characteristics of the strand.

It has now been discovered that it is possible, by characterizing the surface of an extruded strand of a material, to determine the rheological properties of the material therefrom, and to use the properties so as to predict the processability of the material in an operation which shapes the material into a finished article, or which forms the article for an intermediate stage in its production.

Despite the cause of surface variations in the extruded strand, the method and apparatus of the invention provide a rapid, accurate assessment of the nature and type of surface variations so as to enable analysis of the rheological properties of the extruded material.

Extrusion of a continuous strand of material can be accomplished using any device capable of expressing the material through an orifice or die under controlled temperatures and shear rates. The shear rate will be determined by the effect of the shape of the orifice or die, and by the rate at which the material is expressed therethrough. The known Capillary Rheometer is especially effective for this purpose, and is preferred. Its drive system is controlled so as to drive the crosshead at a constant rate independent of the loading effects of the material under test. By means of heating elements, insulation of the sample chamber and thermostatic controls the sample can be maintained at a set temperature. A pressure transducer in the barrel can provide a constant measure of the applied stress.

For measuring the diameter of the extruded strand any means may be employed which yields a series of accurate diameter measurements for the duration of the test. Particularly preferred for this purpose is the optical measuring apparatus disclosed and claimed in U.S. Pat. No. 4,037,968, the disclosure of which is incorporated herein by reference. This apparatus comprises a narrow beam of parallel light which scans an object which is optically located between the edges of an aperture. The light passing through the aperture is detected, and electrical signals generated proportional to the time the object interrupts the light are corrected for variations in the sweep velocity, to provide a signal representative of the width of the object independent of its position in the aperture.

The variations in the strand diameter are interpreted so as to provide a characterization of the surface of the strand. Interpretation of these variations can be done in a variety of ways so as to provide an insight into the nature of the strand surface. For example, the peak values of the diameter can be measured, both high and low values, to derive a measure of the extremes of surface irregularities.

By counting over a time span the number of diameter values which exceed a given variation (both above and below average) by a nominal amount, a measure of the frequency of significant peak values can also be determined. The average diameter of the strand can also be calculated and expressed either as an average diameter value, or, when related to the diameter of the orifice, as an average die-swell value.

In a similar manner, other derivations can be made from the plurality of diameter values so as to characterize the surface of the strand. For example, the standard deviation of the values from the mean can be calculated, and the frequency of the values which exceed a predetermined difference from the standard deviation can be calculated. This frequency can also be employed to characterize the strand surface.

Thus, any mathematical analysis of the diameter values can be useful to provide a tool by which the strand surface can be characterized.

Once a characterization of the surface of the strand has been made, rheological data can be derived therefrom. By analysis of the surface characteristics of the strand as variously derived, an insight into the properties of the material can be gained. The various methods of characterizing the surface, used in combination with each other, provide data by which to compare standard materials with the test material and thus predict how the test material will behave in processing through a wide variety of manufacturing operations.

For example, the scorch behavior of a compounded vulcanizable elastomer can be evaluated by comparing data on the die-swell, surface fracture frequency and peak diameter values with these values for a known material which processes well. The gross scorch time for the compound will be indicated by the rise in the average diameter value, as die-swell increases. The onset of micro-scorch precedes gross scorch in time, and will be signalled by an increase in both peak values and surface fracture frequency. Often in production situations a fully compounded vulcanizable elastomer is stored for a period of several days at room temperature before it is finally processed into a finished rubber article. Successive testing of such a compound over this period by the method of the invention will provide insight into its production behavior on prolonged storage.

In a similar manner, the macrostructure of a "raw", uncompounded elastomer can be evaluated. Diameter values for an extrudate are obtained as before, and analyzed to characterize the surface of the extrudate strand. Parameters such as surface fracture frequency and die-swell can give evidence of the degree of branching in the elastomer chains, gel content and molecular weight distribution. As before, the values obtained for these parameters can be compared with known values for similar elastomer samples. In this way, the method and apparatus can be used in quality control by manufacturers of elastomers, as well as those who fabricate articles from elastomers.

The apparatus of the invention, described in detail infra, comprises means to extrude a continuous strand of the material to be examined, means to measure the diameter of the strand, and means to interpret a plurality of values of strand diameter so as to derive rheological data therefrom.

BRIEF DESCRIPTION OF THE DRAWINGS

FIG. 8 is a schematic diagram of the system which converts the analogue input of strand diameter into outputs characterizing the surface of the strand.

FIG. 9 is a schematic block diagram showing further processing of the outputs of FIG. 8.

DESCRIPTION OF THE PREFERRED EMBODIMENTS

Figure 1:
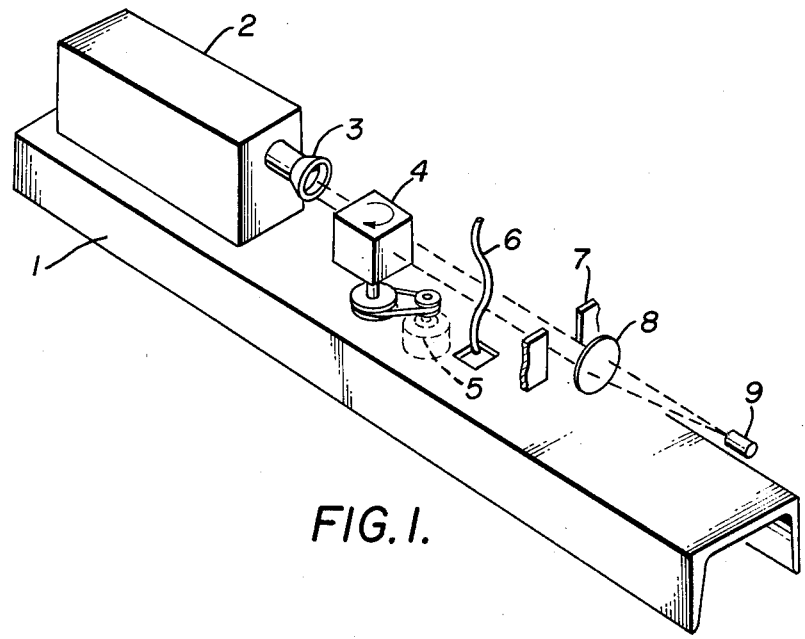
FIG. 1 is a schematic perspective view of a device for optically measuring the diameter of an extrudate strand.

Referring to FIG. 1, it shows the various elements of the optical die swell system supported by mounting frame 1. A laser 2, mounted thereon, produces a narrow beam of parallel light which is passed through a condensor/collimator 3. A cube prism 4 is rotated at substantially constant speed by motor 5. The prism maintains parallelism of the light and its rotation produces a sweep of a refracted beam of parallel light across the object 6 which in the case illustrated is continuous strand extruded from a Capillary Rheometer. The system is especially valuable for measuring small dimensions larger than can be measured by diffraction techniques and, in general, excellent results are obtainable over the range of about 0.01 inch to 1.0 inch (0.0254–2.54 cm). The beam also sweeps across measuring space 7 which is an aperture within which the strand 5 is disposed. The aperture and, hence, the lateral active area may be 0.5 inch (1.27 cm) in a typical example but the system is not limited to this dimension. The light through the aperture passes through condensor lens 8, and the emerging beam is focused onto a photodetector 9.

Compensation for variation of position of the object within the measuring space as well as for motor speed variation is provided by a dual integration technique. To eliminate effect of motor speed variation, the electrical output (composite pulse) from the photodetector is separated into a long pulse determined by the dimensions of the aperture and a short pulse determined by the shadow of the strand or object to be measured. The long pulse starts and stops the integration of a fixed reference current from a constant current source. More particularly, the modulated current from the constant current source is gated into an aperture integrator with the long pulses created as the laser beam strikes the leading and trailing edges of the aperture. Since the aperture width is constant, the voltage output of the aperture integrator is inversely proportional to the average sweep speed of the laser beam or motor speed. Such output voltage inversely proportional to motor speed is the input to a differential amplifer which provides a current to an extrudate integrator. Because the current integrated in the extrudate integrator is inversely proportional to motor speed by the same ratio as the current integrated in the aperture integrator, the output voltage of the extrudate integrator is proportional to the strand diameter only and is not affected by motor speed. Therefore, motor speed variations have no effect on this voltage.

Figure 2:
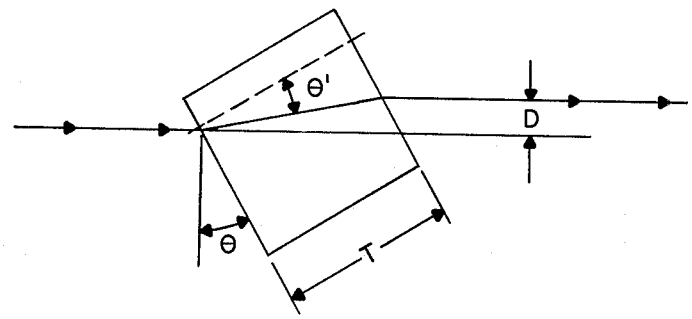
FIG. 2 is a diagram showing the displacement of a light beam caused by refraction of the light beam by a cube.

There is a geometrical velocity error created by the refraction of a light beam by a rotating cube. Refraction of a light beam by a cube creates a displacement proportional to the rotational angle of the cube as illustrated in FIG. 2. If D represents the linear displacement of the incident beam, $$D = T \sin \theta \left[ 1 - \frac{\cos \theta}{N \cos \theta'} \right]$$

where T is the length of the side of the cube, $\theta$ is the angle of incidence, $\theta'$ is the angle of deviation and N is the refractive index of the cube. The rate of change of displacement of the beam sweeping across the measuring space is not constant for a constant angular velocity but follows an approximate sine function. An approximate sine function (compensation signal) representative of rate of change of displacement of the beam is generated in synchronization with the aperture pulse from the pulse separator. This compensation signal is integrated in synchronization with a sweep compensation integrator and in synchronization with the shadow of the strand to provide offset correction for the strand integrator in relation to the position of the strand in the aperture. The outputs from the extrudate integrator and the sweep compensation integrator are summed to provide an output voltage proportional to strand diameter, which is not affected by motor speed fluctuation or position of the strand within the aperture. Effectively, the strand can move to any position in the measuring area without substantially affecting the measurement accuracy. Similarly, the strand can move in line with a receiving beam and because the spot size is constant, and the scanning beam rays are parallel, movement in this plane will not affect accuracy. The analogue voltage can then be scaled to provide dimensions in English units or metric units with a single output amplifier and panel meter.

Figure 3:
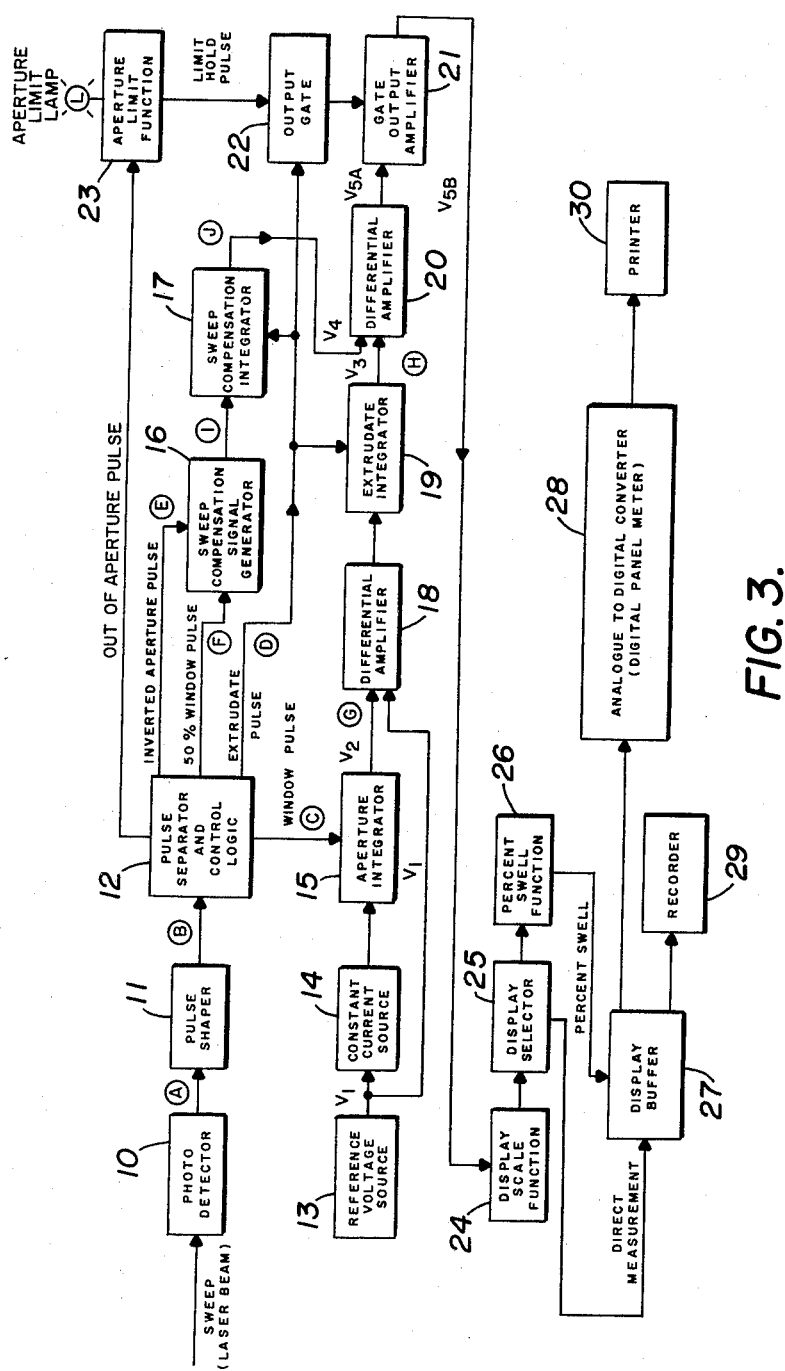
FIG. 3 is a block diagram showing a preferred system for processing the light detected through the measuring space by a photo detector.
Figure 4:
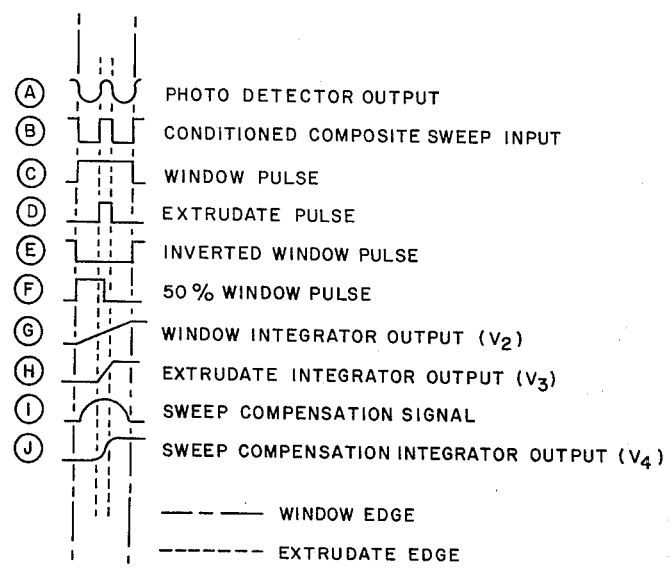
FIG. 4 is a representation of the pulse shapes involved in the system of FIG. 3.

Referring to FIGS. 3 and 4, the photodetector 10 generates a signal represented by A of FIG. 4. The illumination detected by the photodetector as the beam crosses the edge of the measuring space (aperture) from the nonilluminated to the illuminated direction (rises rapidly to a maximum and then falls to a minimum again as the beam passed one edge of the strand in the illuminated to nonilluminated direction. It again rises rapidly to a maximum as the beam crosses the other edge of the strand in the nonilluminated to illuminated direction. Finally, the illumination detected by the photodetector falls once more to a minimum as the beam crosses the other edge of the aperture in the illuminated to nonilluminated direction. The dashed vertical lines on FIG. 4 correspond to the aforementioned four edges.

Pulse shaper 11 converts the photoelectric output A to squared pulse B so as to provide a definite low-high, high-low sequence each time the beam crosses an edge, whether it be edge of the aperture or the edge of the strand. The pulse separator and control logic 12 provide a pulse C designated "aperture pulse" representative of the width of the aperture (aperture and window are herein used synonymously) and a pulse D representative of the width of the strand designated "extrudate pulse". It follows from FIG. 2 that the sweep velocity reaches a minimum halfway between the edges of the aperture. Since the rate of change of displacement or linear velocity is greatest at the aperture edge and progressively diminishes to the center from either edge, the correction is directly proportional to distance from an edge. For synchronization it is convenient to generate an inverted aperture pulse E and a 50% aperture pulse F because the correction is symmetrical around the midpoint of the aperture.

The aperture pulse is used to start and stop the integration of a constant current 14 derived from a fixed constant voltage source 13. Since the aperture width is constant, the voltage output G of the aperture integrator 15 is inversely proportional to the average sweep speed of the laser beam determined by motor speed. This output voltage, inversely proportional to sweep speed, is supplied to one input of differential amplifier 18. Such input ($V_2$) is compared with the reference voltage ($V_1$) from constant voltage source 13 and the algebraic sum (directly proportional to average sweep speed) supplied as the input to the extrudate integrator 19. The extrudate integrator 19 is started and stopped by the extrudate pulse D. The current is inversely proportional to sweep speed by the same ratio as the extrudate pulse width, therefore, the output of the extrudate integrator 19 is proportional to strand diameter only and not affected by average sweep speed.

A sweep compensation signal generator 16 generates a compensation signal in synchronization with the inverted aperture pulse E and the 50% aperture pulse F supplied from the pulse separator 12. This compensation signal I is integrated by the sweep compensation integrator 17 in synchronization with the extrudate pulse D. Pulse E represents the full aperture size but is inverted to afford the polarity which will enable it to perform its synchronizing function. Pulse F represents one half the aperture pulse and is used to determine the midpoint of the aperture. The leading edge of the inverted aperture pulse triggers pulse F, causing voltage to ramp up over the span of pulses F and ramp down again to zero at the end of the pulse E. The triangular wave thus formed is shaped into ½ a sine wave. When triggered by pulse F and the leading edge of the aperture, the voltage builds up at a rate approximating a sine wave function to a maximum at the point corresponding to the midpoint of the aperture then drops again to zero at the trailing edge of the aperture.

The output of the extrudate integrator 19 and the sweep compensation integrator 17, waveforms H and J, are supplied to a differential amplifier 20 to be algebraically summed to provide an output voltage ($V_5A$) proportional to extrudate diameter and not affected by position of extrudate in the aperture or speed fluctuation.

The output of the differential amplifier 20 is supplied to the gated output amplifier 21, which performs a sample and hold function following each extrudate pulse D except when a limit hold pulse inhibits the output gate 22. The out of aperture pulse from the pulse separator 12 is initiated whenever the extrudate pulse D is missing in the composite pulse B input to the pulse separator 12. This condition whenever the motion of the extrudate would cause it to appear (optically) to contact the edge of the aperture or to move completely out of the aperture. The out of aperture pulse triggers the aperture limit function 23 which latches into a hold condition, illuminating the aperture limit lamp L and inhibiting the output gate 22. The limit hold condition remains latched until a valid extrudate pulse appears. This latching function insures that only valid measurements are applied to display (readout) circuits.

The signal $V_5B$ from the gated output amplifier 21 is applied to the display scale function 24 which scales it in English or metric engineering units. The scaled signal from the display scale function 24 is selected by the display selector 25 for display as either direct measurement of the extrudate diameter or percent swell based upon die (orifice) diameter. The percent swell function 25 subtracts the orifice diameter from the calibrated input and converts the difference into percent swell. The output from the percent swell function 26 or the output from the display scale function is then applied to the output buffer 27 for electrical isolation and impedance matching for display devices. One output is applied to an analogue to digital converter 28 (digital panel meter) and another to recorder 29. The digital panel meter may then drive printer 30 which prints out the selected parameter in digital units. The resultant display can thus be switched at will from strand diameter, for example, in thousandths of an inch or in millimeters to percent die swell.

Although the scanning beam diameter is reduced from approximately 0.40 inches (1.016 cm) to 0.005 inches (0.0127 cm) by the condensing/collimating lens combination, there is still a potential error caused by part of the beam passing the edge of the object to be measured. Previous techniques have used a variable threshold level set for each nominal measurement or a zero crossing of the second differential or the photodetector. The former technique is effective only over a narrow range of diameters near that of a set nominal and the latter technique requires sophisticated electronics. Measurements with calibrated gauge pins have shown this beam diameter error to be a constant value for any specific beam and photodetector combination. Withe the above-mentioned reference integration circuit, a slight offset of the modulated reference current will effectively compensate for this beam diameter error for all diameters within the capacity of the system.

Figure 5:
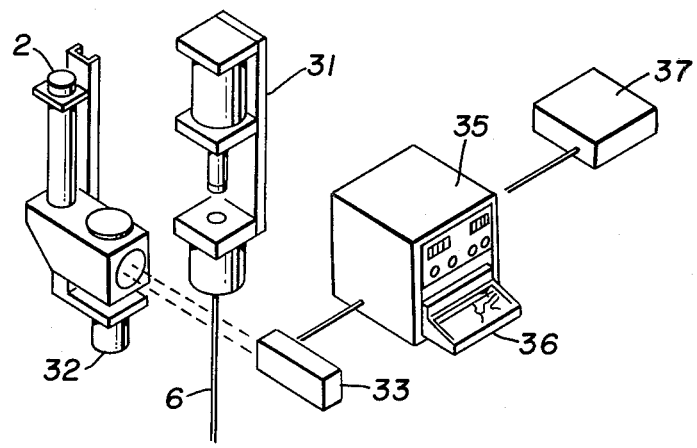
FIG. 5 is a perspective layout for strand diameter measurement comprising a Capillary Rheometer combined with the optical measuring device.

FIG. 5 illustrates a system layout for evaluating properties of plastic substances by combining a capillary rheometer with the optical measuring apparatus as a strand diameter measuring device. An automatic Capillary Rheometer 31 extrudes from its orifice the strand 6 in the path of parallel light rays from the laser 2. The laser is vertically mounted and the strand extruded vertically but the collimator rotating cubic prism assembly 32 directs the light horizontally through a collimator and rotating prism so as to sweep the light rays across the strand and across the aperture in the photodetector assembly 33. The collimator, rotating cube assembly corresponds to collimator 3 and rotating cube 4 of FIG. 1 and contains in addition a front surface mirror to direct the laser beam. The photodetector assembly contains an aperture, condensing lens and photocell and corresponds to aperture 7, condensing lens 8 and photodetector 9 of FIG. 1. The strand dimensional monitor electronics 35 carry out the functions of elements 11–29 of FIG. 2 and in addition may contain the electronics for the conventional Capillary Rheometer. Thus, the strip chart recorder 36 may chart dimensions of the extrudate or percent die swell as one tracing and rate of shear or stress as the other. The data printer 37, which may be a teletype or the like, prints out such digital readouts as are desired.

Figure 6:
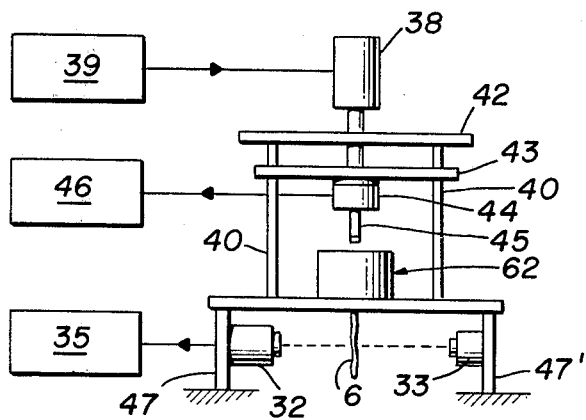
FIG. 6 is a schematic layout of another embodiment of the combination of the Capillary Rheometer with the optical measuring device.

The components of a system for measuring processability will be more clearly understood by referring to FIG. 6 which relates the electronics to a capillary rheometer. The drive system for the capillary rheometer 38 preferably comprises a closed loop servo hydraulic cylinder, controlled by digital pulses supplied by the drive electronics programmer 39. For example, the drive system may comprise an Olsen Linear Electrohydraulic Pulse Drive Model No. LS300 manufactured by Olsen Control, Inc., Bristol, Conn., and described in U.S. Pat. No. 3,899,956. The control may be a microcomputer such as the MCS-40 microcomputer available from Intel Corporation. In this embodiment, guide rods 40 mounted between base support 41 and top support 42 guide the movement of a constant rate crosshead 43. The drive system drives the crosshead at a constant rate independent of loading effects of the material under test. The digital drive enables the selection of either a predetermined single constant rate of crosshead travel or a controlled continuous sweep of different rates of crosshead travel over a predetermined range as provided by the programmer.

Figure 7:
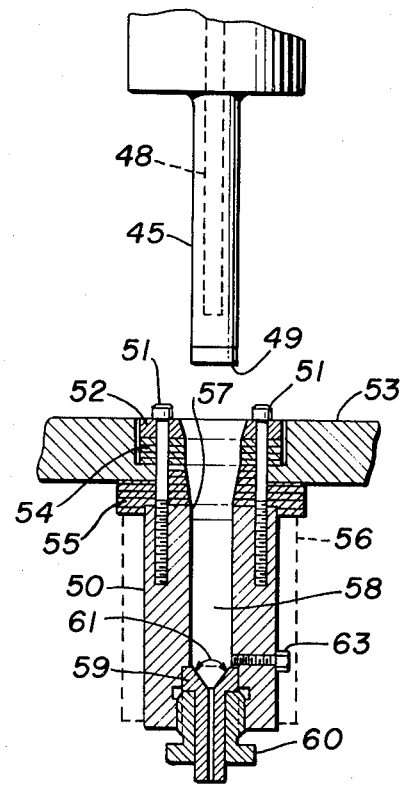
FIG. 7 is a cross-sectional view of the piston and cylinder of the Capillary Rheometer.

A strain gauge load cell 44 is mounted on the crosshead and suitably coupled through heat insulation to a temperature-controlled piston 45. The stress signal from the load cell is processed by the stress electronics 46 and cen be recorded as hereinafter explained. Alternatively, a pressure transducer 63 may be mounted at the base of the sample test cavity but above the entrance to the capillary orifice as shown in FIG. 7. The laser scanning monitor 32 is the collimator rotating prism assembly previously described and is under control of the strand dimensional monitor electronics 35. It is generally in a fixed position, usually 3–300 millimeter from the orifice outlet, at the base of the capillary rheometer on support member 47. Photodetector 33, mounted on opposite support member 47, views extrudate 6 extruded from the temperature-controlled barrel and orifice assembly indicated generally as 62.

In another embodiment advantageous for determining rapidly swelling materials, the scanning assembly is continuously raised and lowered as by an electrically driven motor, (not illustrated). For example, in a typical case, the scanning assembly might be raised and lowered over a range of 3–50 mm from the orifice outlet. The strand dimension at the beginning of the cycle 3 mm. from the orifice outlet, and the maximum strand dimension during the cycle, provide a convenient basis for determining swelling rate. The distance from the orifice at which the maximum occurs, which will of course be the maximum distance from orifice outlet if swelling continues over the entire range of observations, can be readily determined from the continuous graphical recording of dimensions. That distance combined with knowledge of the rate at which the material is extruded permits calculations of the time to achieve maximum swelling and this together with knowledge of extent of swelling over run time permits precise determination of the rate of swelling of the test material.

FIG. 7 is a cross-sectional view of the piston and cylinder of the preferred capillary rheometer. Piston 45 contains a cartridge heater 48 and comprises a terminal section 49, machined to engage the barrel 50 in close tolerance, and roughened at the tip to engage the test sample. A continuous groove is machined into the tip. The root mean square depth of the grooves is typically in the range of 125 to 250 micro inches (0.375–0.653 cm) as measured by a profilometer. The sample residue clings to the piston surface so roughened and is easily removed upon raising the piston. The piston displacement range may typically be 0.05–5.0 in. per minute (0.127–12.7 cm.) per minute ±1%, and the load capacity range is 0–6200 pounds (0–2813 kg.).

In the cylinder section cap screws 51 hold clamp ring 52, support plate 53 and insulators 54 and 55. Heater 56 surrounds the barrel and controls temperature independently of the piston to precise limits over the range from slightly above ambient temperatures to 550° F. (287.78° C.). The dimensions of the barrel section 50 are designed to permit easy loading of the sample. Typically, the diameter is ¾ inch (1.905 cm). The clamp ring 52 has about a 15 degree entrance angle and the barrel has a piston lead-in taper 57 which may be 3°, for example, to facilitate piston entrance and sample loading. The straight section of the barrel comprises the sample-holding portion 58 which in a typical case may be 2 in. (5.08 cm). At the base of the barrel 50 but above the entrance to the capillary orifice is the aforementioned pressure transducer 63. For some polymers a pressure transducer indicates sample stress more accurately than a load cell shown in FIG. 6. Certain polymers of which natural rubber is an example tend to stick to the barrel. Because of the resulting pressure loss, the load applied by the piston may not be an accurate measure of the stress on the material at the bottom of the barrel. The piston automatically stops when it reaches the extremity of the sample holding portion to avoid injury to the capillary.

Capillary body 59 is held in place by retaining nut 60. A number of different orifices are provided and can be readily interchanged. The entrance angle 61 can vary but will generally be 60°–90°. It will be noted that an entrance angle of 90° as illustrated means that each side of the cone-shaped entrance section makes an angle of 45° with its base. If desired, a compound entrance angle may be used such as 90° and 60° with the entrance area as much as 100° of the piston surface area. The capillary orifices typically have a minimum of 20:1 length over diameter ratio and nominal diameters of 0.020, 0.040, 0.080 and 0.100 inches (0.0508, 0.1016, 0.2032 and 0.254 cm).

Referring again to FIG. 3, a preferred measure of strand diameter is signal $V_5B$ generated at gated output amplifier 21. By means of the operations set out in FIG. 3, the optical measure of the strand diameter is converted to an analogue signal, and the measuring errors are corrected. This analogue signal is input to the circuitry shown in FIG. 8.

FIG. 8 depicts a preferred method and apparatus for interpreting the variations in strand diameter, wherein electronic integrator $A_1$ is controlled by two field-effect transistors ($S_1$ and $S_2$) so that the integration of the diameter signal will occur only during a period determined by the extruder drive pulses. Integrator $A_1$ sums the resultant readings corresponding to a given number of pulses (ten is used, as a practical standard). The control is set up to sequence the operation of $S_1$, $S_2$ and $S_3$ in accordance with the timing diagram in FIG. 10. At the end of ten pulses the sum of $A_1$ is transferred to the "sample and hold" circuit $A_2$. The gain of $A_2$ is set to one tenth the output of $A_1$, thus the signal at Output 1 represents the average of ten incremental readings, and will be referred to as the "incremental average."

Circuit $A_3$ is another integrator, whose integrator period is controlled by $S_4$ such that the values of $A_2$ are summed after every 10th pulse. The output of $A_3$ will therefore represent the sum of the incremental averages. $A_4$ is a programmable "sample and hold" circuit. Its function is to give an output equal to $\Sigma n$ samples divided by n, that is, the *overall* average readings. This signal is obtained at Output 2.

$A_5$ operates an anlogue comparator, the output of which will display the difference between the strand diameter readings and the incremental average diameter at Output 1. Two Schmitt triggers are connected to the output of $A_5$ and will detect the positive and negative excursions about the incremental average value. The triggers are set so that at a certain given threshold voltage they will rapidly change state and will return to the original state when the input voltage drops below a threshold voltage. In this way, at Output 5 a pulse train is derived representing the surface perturbations. A counter displays the frequency of perturbations which are greater in magnitude than those corresponding to the threshold voltage.

Maximum diameters are also measured, using peak detectors which continually record maximum excursions from the average diameter. These values are obtained at Output 4.

FIG. 9 shows the steps which convert Outputs 2 and 4 from analogue to digital mode, and, together with Output 3, feed them to a limit comparator which has been programmed to specific limits. Go/no-go indicators show the acceptability of the outputs, and the values are then printed.

Figure 10:
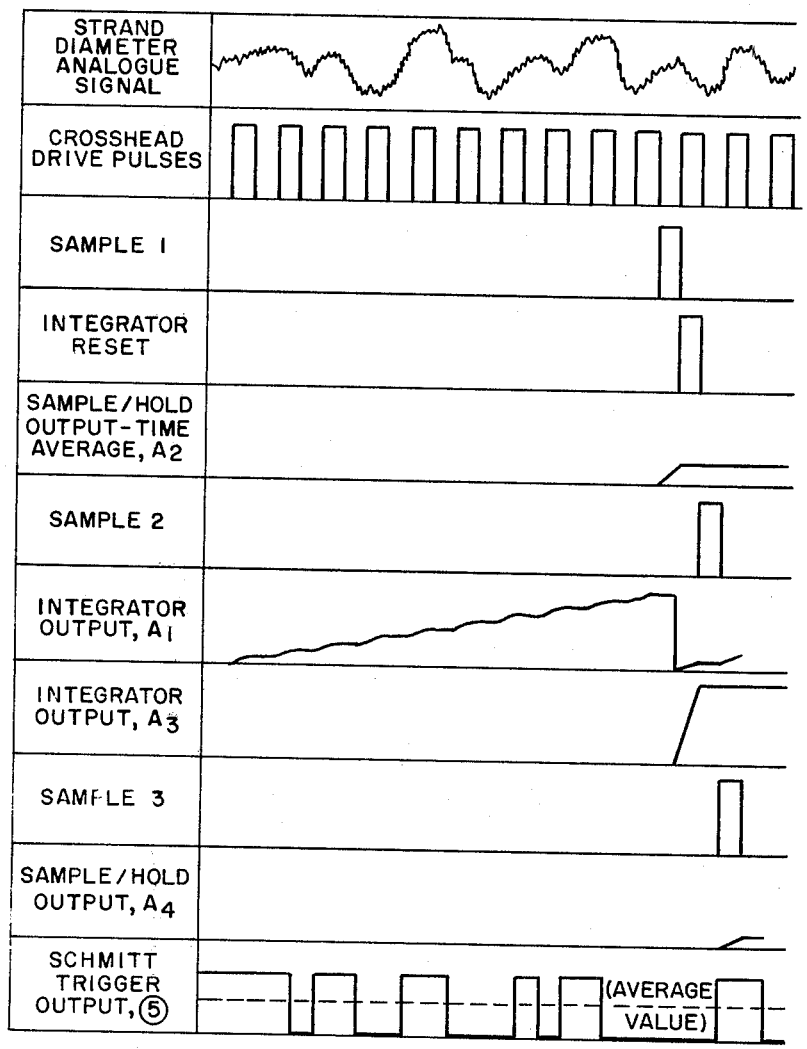
FIG. 10 is a representation of the pulse shapes involved in the system of FIG. 8.

In FIG. 10, pulse diagrams show the relationship of the various outputs to the analogue diameter signal.

EXAMPLE I

A rubber compound was made up according to the following recipe, in which all parts are by weight:

|  | | | |
|---|---|---|---|
| Master Batch | Natural Rubber (SMR 5CV) | 100 | |
| | Carbon Black (N330-HAF) | 50 | |
| | Oil (Dutrex 729) | 3 | |
| | Zinc Oxide | 5 | |
| | Stearic Acid | 2 | |
| | Antiozonant (Santoflex ®IP) | 1 | |
| | Antioxidant (Flectol ®Flakes) | 1 | |
| Final | Sulfur | 2.5 | |
| | Accelerator (Santocure ®) | 0.6 | |

The batch size was 20 kg.

The ingredients were charged, in the order named, to a Shaw K-2A Intermix laboratory mixer and mixed at 25 RPM rotor speed and 50 psi ram pressure. Final dump temperature was 163° C.

A 12.5 gram sample of the compound was charged to the barrel of the capillary rheometer, maintained at 284° F.(140° C.). The piston was driven at the rate of 0.05 inch per minute (1.27 mm/min.), extruding a strand of rubber through an orifice of 0.04 inch diameter (1.02 mm). The strand diameter was measured optically, and stress and strand diameter readings were continuously recorded on a strip chart.

Figure 11:
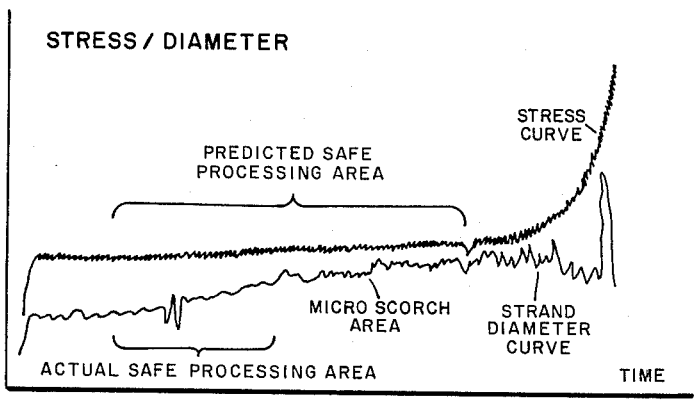
FIG. 11 shows diameter and stress curves for a vulcanizable elastomer.

A separate determination of the cure rate of the above compound, as measured on a Monsanto Processability Tester had indicated the processing range to be from about one minute to about five minutes, at which time the bulk viscosity of the compound began to rise sharply. Visual analysis of the strand diameter tracing on the chart as depicted in FIG. 11, however, showed onset of an increased "roughness" of the strand surface at about 2.8 minutes. This phenomenon was felt to indicate that "micro scorch" was beginning, and that the onset of local precure had occurred well before the bulk viscosity measurement indicated that scorch had started.

It was desired to obtain a numerical expression for the degree of roughness of the strand which would provide more precise information on micro-scorch than could be obtained by visual analysis of the curve. By means of the circuitry shown in FIG. 8 the strand diameter signal was interpreted to give values for average strand diameter, peak-to-peak diameter variation and the frequency of significant perturbations. While the average strand diameter showed no sharp change at the onset of micro scorch, the sudden increase in the other two values clearly indicated that changes occurred in the rheological behavior of the compound at that point.

EXAMPLE II

In another experiment, a natural rubber compound was prepared according to the following formulation in which all parts are by weight:

Natural Rubber (SMR 20, unmasticated): 100
Carbon black (ISAF - N 220): 45
Oil (Dutrex 729): 5
Zinc Oxide: 5
Stearic Acid: 3
Santoflex ® 13 antiozonant: 2
Sulfur: 2.5
Santocure ®MOR accelerator: 0.5

All ingredients, except sulfur and accelerator, were charged to the Shaw Intermix mixer described above. After 2¼ minutes of mixing, the batch was dumped at 155° C. and a sample was withdrawn, identified as "master batch."

When the initial batch had cooled to room temperature, it was again charged to the mixer, mixed for two additional minutes and dumped at a temperature of 162° C. A sample was withdrawn and identified as "remill."

After the batch had again cooled to room temperature it was charged to the mixer, the sulfur and accelerator added, and mixing was continued for 3 minutes, the batch being dumped at 98° C. A sample was again taken, and identified as "final mix."

Figure 12A:
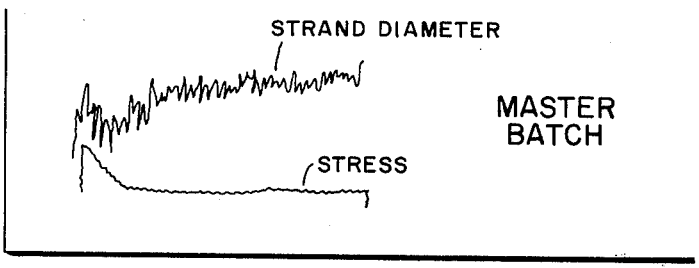
FIGS. 12a, 12b and 12c show diameter and stress curves for a rubber compound through three milling steps.
Figure 12B:
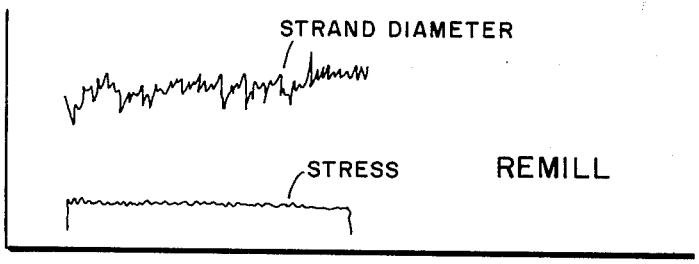
Figure 12C:
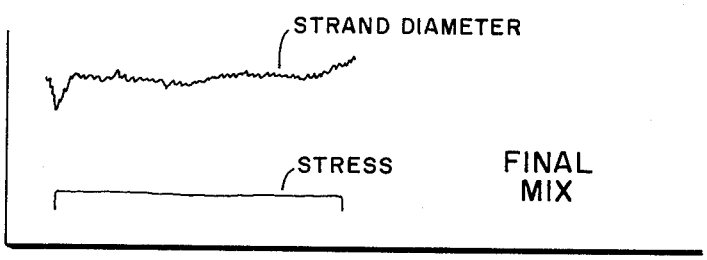

The three samples were each charged in turn to the barrel of the capillary rheometer as before, and an extruded strand was produced in each instance, and optically measured. As shown in FIG. 12, the curves of stress and strand diameter were recorded on strip charts.

In addition, the analogue signals representing the strand diameter were electronically interpreted to yield values for average strand diameter, peak-to-peak excursions and frequency of perturbation. The derived values were as follows:

| | Av'g. Strand Diameter, % of Orifice Size | Peak-to-Peak; % of Orifice Size | Frequency |
|---|---|---|---|
| Master Batch | 123 | 5% | 0.3 sec.$^{-1}$ |
| Remill | 125 | 6% | 0.3 sec.$^{-1}$ |
| Final Mix | 123 | 0.5% | 1.0 sec.$^{-1}$* |

*the threshold limit for significant peaks was lowered for this reading, in order to obtain a number value.

Analysis of the values shows that the average strand diameter increased and then went back to its previous level. The peak-to-peak value increased slightly with mixing time, then dropped off sharply in the final mix. This drop-off is significant of the good dispersion realized in the final mix. The earlier batches show the effect of incomplete dispersion, with the rough surface of the extruded strand showing up clearly in the peak-to-peak values.

In a similar manner, raw, uncompounded polymers can be extruded from the capillary rheometer, and the strand diameter measured to produce a series of diameter values. Analysis of these diameters values can be performed so as to characterize the strand surface and thereby provide insight into the macromolecular structure of the polymers. By heating the polymers the effect of heat on the polymer structure can also be measured. As noted above, the method and apparatus of the invention is particularly effective in predicting the processability of vulcanizable compounded elastomers. However, other extrudable materials, such as thermoplastic elastomers and other organic polymers can be effectively evaluated, as well. Thus, compounded and uncompounded natural or synthetic rubber such as SBR, polyisoprene, butyl, polychloroprene, nitrile, EPDM or polybutadiene can be tested, and other thermoplastic polymers and blends of polymers. The invention is also useful in evaluating thermosetting materials such as polyurethanes and polyolefins, plasticized polyvinylchloride, polyphosphazenes, impact-modified polystyrene, SAN and ABS plastics and other extrudable materials.

The embodiments of the invention in which an exclusive property or privilege is claimed are defined as follows:

1. The method of measuring the rheological properties of an extrudable material comprising the steps of (a) extruding a continuous strand of the material under controlled conditions of temperature and shear rate or shear stress, (b) measuring the diameter of the strand periodically to provide a plurality of instantaneous diameter values, (c) averaging the instantaneous diameter values over a finite number of such values to obtain an average diameter figure, (d) measuring the frequency of those instantaneous values which depart from the average diameter figure by more than a given amount, and (e) comparing the frequency thus obtained with a predetermined standard.

2. The method of claim 1, wherein the diameter of the strand is measured optically.

3. The method of claim 1, wherein the diameter values are expressed in an analogue signal.

4. The method of measuring the rheological properties of an extrudable material comprising the steps of (a) extruding a continuous strand of the material under controlled conditions of temperature and shear rate or shear stress, (b) measuring the diameter of the strand periodically to provide a plurality of instantaneous diameter values, (c) calculating the magnitudes of the peak-to-peak differences in diameter values, and (d) comparing the magnitudes thus calculated to a predetermined standard.

5. The method of claim 4, wherein the diameter of the strand is measured optically.

6. The method of claim 4, wherein the diameter values are expressed in an analogue signal.

7. The method of measuring the scorch time of an extrudable vulcanizable rubber compound comprising the steps of (a) extruding a continuous strand of the compound under controlled conditions of temperature and shear rate or shear stress, (b) measuring the diameter of the strand from time to time to provide a plurality of diameter values, (c) characterizing the diameter values as to the magnitudes of the peak-to-peak differences therein, (d) comparing the magnitude of the peak-to-peak differences with a predetermined standard, and (e) determining the time at which the said magnitude exceeds the predetermined standard.

8. The method of claim 7, wherein the diameter of the strand is measured optically.

9. The method of claim 7, wherein the diameter values are expressed in an analogue signal.

10. Apparatus for measuring rheological properties of an extrudable material, comprising in combination:

(a) an extruder capable of extruding a strand of the material at controlled temperature and shear rate, (b) means to measure the diameter of the strand thus formed, (c) means to average diameter readings over a plurality of diameter measurements, and (d) means to record maximum excursions from the average diameter.

11. Apparatus according to claim 10, wherein the means to measure the diameter of the strand is optical means.

12. Apparatus according to claim 11, wherein the optical means includes a laser beam.

13. Apparatus for measuring rheological properties of an extrudable material, comprising in combination:

(a) an extruder capable of extruding a strand of the material at controlled temperature and shear rate, (b) means to measure the diameter of the strand thus formed, (c) means to average diameter readings over a plurality of diameter measurements, and (d) means to record the frequency of diameter reading excursions having a given value above or below the average diameter.

14. Apparatus according to claim 13, wherein the means to measure the diameter of the strand is optical means.

15. Apparatus according to claim 14, wherein the optical means includes a laser beam.

* * * * *